US010633629B2

(12) United States Patent
Joustra

(10) Patent No.: US 10,633,629 B2
(45) Date of Patent: Apr. 28, 2020

(54) BACTERIA AND CONSORTIA FOR THE REDUCTION OF AMMONIA AND/OR METHANE EMISSION IN MANURE OR SOIL

(71) Applicant: Rinagro B.V., Piaam (NL)

(72) Inventor: Rinze Joustra, Piaam (NL)

(73) Assignee: Rinagro B.V., Piaam (NL)

( * ) Notice: Subject to any disclaimer, the term of this patent is extended or adjusted under 35 U.S.C. 154(b) by 0 days.

(21) Appl. No.: 14/654,262

(22) PCT Filed: Dec. 23, 2013

(86) PCT No.: PCT/NL2013/050949
§ 371 (c)(1),
(2) Date: Jun. 19, 2015

(87) PCT Pub. No.: WO2014/104883
PCT Pub. Date: Jul. 3, 2014

(65) Prior Publication Data
US 2016/0333306 A1 Nov. 17, 2016

(30) Foreign Application Priority Data

Dec. 31, 2012 (NL) ..................................... 2010074

(51) Int. Cl.
| | |
|---|---|
| *C12N 1/20* | (2006.01) |
| *C12R 1/01* | (2006.01) |
| *C05F 3/00* | (2006.01) |
| *C05F 11/08* | (2006.01) |
| *C02F 3/34* | (2006.01) |

(52) U.S. Cl.
CPC .................. *C12N 1/20* (2013.01); *C05F 3/00* (2013.01); *C05F 11/08* (2013.01); *C12R 1/01* (2013.01); *C02F 3/341* (2013.01); *Y02A 40/205* (2018.01); *Y02E 50/343* (2013.01); *Y02P 20/145* (2015.11); *Y02W 30/47* (2015.05)

(58) Field of Classification Search
None
See application file for complete search history.

(56) References Cited

U.S. PATENT DOCUMENTS

| | | | | |
|---|---|---|---|---|
| 4,264,448 | A | 4/1981 | Bodenrader | |
| 5,198,252 | A * | 3/1993 | Simsa | C05F 17/00 426/52 |
| 5,945,333 | A * | 8/1999 | Rehberger | A01N 63/00 119/171 |
| 6,025,187 | A | 2/2000 | Penaud | |
| 7,858,336 | B1 * | 12/2010 | Garner | C12R 1/23 435/243 |
| 2009/0275109 | A1 * | 11/2009 | Bellot | A01K 1/0152 435/252.5 |
| 2011/0000851 | A1 * | 1/2011 | Vanotti | C02F 3/341 210/620 |

FOREIGN PATENT DOCUMENTS

| | | |
|---|---|---|
| RU | 2322427 C1 | 4/2008 |
| WO | WO2007072935 A1 | 6/2007 |
| WO | WO 2012/101528 A2 | 8/2012 |

OTHER PUBLICATIONS

Barton, H.A. et al. 2007. The impact of host rock geochemistry on bacterial community structure in oligotrophic cave environments. International Journal of Speleology 36(2): 92-104. specif. pp. 93, 97, 102.*
McCrory, D.F. et al. 2001. Additives to reduce ammonia and odor emissions from livestock wastes: a review. Journal of Environmental Quality 30: 345-355. specif. p. 348.*
Kuroda, K. et al. 2004. Isolation of thermophilic ammonium-tolerant bacterium and its application to reduce ammonia emission during composting of animal wastes. Bioscience, Biotechnology and Biochemistry 68(2): 286-292. specif. p. 286.*
Naidu, A.S. et al. 2002. Reduction of sulfide, ammonia compounds, and adhesion properties of Lactobacillus casei strain KE99 in vitro. Current Microbiology 44: 196-205. specif. p. 196, 203.*
Wang, Y. et al. 2009. The effect of probiotic BioPlus2B on growth performance, dry matter and nitrogen digestibility and slurry noxious gas emission in growing pigs. Livestock Science 120: 35-42. specif. pp. 35, 36.*
McCrory, D.F. et al. 2001. Additives to reduce ammonia and odor emissions from livestock wastes: a review. Journal of Environmental Quality 30: 345-355. specif. pp. 345, 348, 351.*
Nielsen, D.S. et al. 2007. *Lactobacillus ghanensis* sp. nov., a motile lactic acid bacterium isolated from Ghanaian cocoa fermentations. International Journal of Systematic and Evolutionary Microbiology 57: 1468-1472. specif. pp. 1468, 1469.*
Thaler, B. et al. 2010. By-product feed ingredients for use in swine diets. National Swine Nutrition Guide Factsheet. PIG Jul. 6, 2001. pp. 1-12. specif. p. 9.*
Hargreaves, J.A. et al. 2004. Managing ammonia in fish ponds. Southern Regional Aquaculture Center. SRAC publication No. 4603. pp. 1-8. specif. p. 1.*
Database EMBL, Uncultured bacteroidetes bacterium clone NMT sF40 16S ribosomal RNA gene, partial sequence, XP002703676, retrieved from EBI accession No. EM_STD:DQ066616, Database accession No. DQ066616 sequence, Jun. 14, 2005.
Database EMBL, Bacterium enrichment culture clone PKWE55-10 16S ribosomal RNA gene, partial sequence, XP002721903, retrieved from EBI accession No. EM_STD:JQ670733, Database accession No. JQ670733 sequence, May 20, 2012.
Chadwick, Emissions of ammonia, nitrous oxide and methane from cattle manure heaps: effect of compaction and covering, Atmospheric Environment (2005), 39(4):787-799.

(Continued)

*Primary Examiner* — Renee Claytor
*Assistant Examiner* — Sharon M. Papciak
(74) *Attorney, Agent, or Firm* — Rudy J. Ng; Bret E. Field; Bozicevic, Field & Francis, LLP

(57) ABSTRACT

The invention is related to a new bacterium comprising a partial 16S rDNA nucleic acid sequence having more than 85% sequence identity to the sequence presented as SEQ ID NO:1, or the complement thereof and a consortium of micro-organisms improving manure or soil.

6 Claims, 1 Drawing Sheet

Figure 1A:
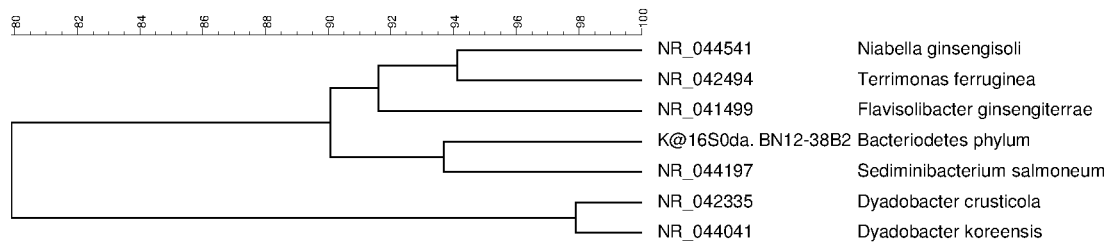
Figure 1B:
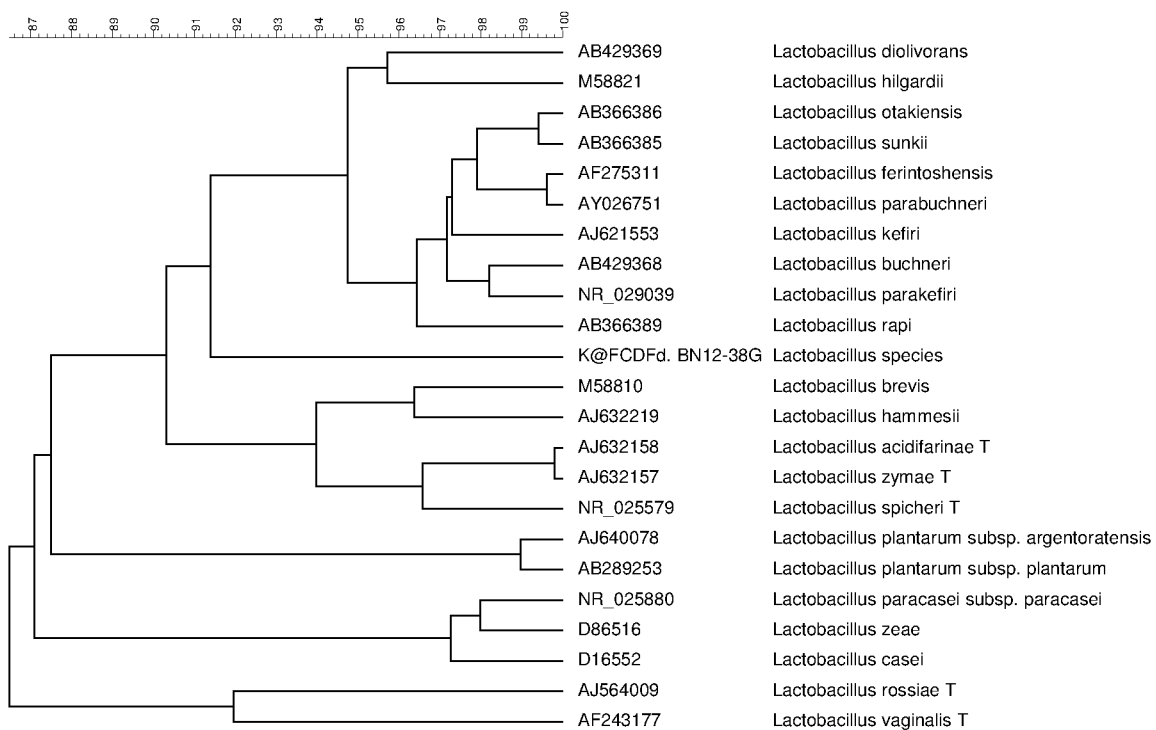

Specification includes a Sequence Listing.

(56) References Cited

OTHER PUBLICATIONS

Melse et al., Evaluation of Four Farm-scale Systems for the Treatment of Liquid Pig Manure, Biosystems engineering (2005), 92(1):47-57.
Mirza et al., Development of a direct isolation procedure for free-living diazotrophs under controlled hypoxic conditions, Appl Environ Microbiol (2012), 78(16):5542-5549.
Wang et al., Microbial community structure in anaerobic co-digestion of grass silage and cow manure in a laboratory continuously stirred tank reactor, Biodegradation (2010), 21(1):135-146.
Janda et al. "16S rRNA Gene Sequencing for Bacterial Identification in the Diagnostic Laboratory: Pluses, Perils, and Pitfalls," Journal of Clinical Microbiology, vol. 45, No. 9, Sep. 2007, pp. 2761-2764.

\* cited by examiner

BACTERIA AND CONSORTIA FOR THE REDUCTION OF AMMONIA AND/OR METHANE EMISSION IN MANURE OR SOIL

This invention is related to new bacteria, a consortium comprising these bacteria and the use of the consortium for reduction of ammonia and/or methane emission in manure.

Manure is organic matter and can be used as organic fertilizer in agriculture. Manure contributes to the fertility of the soil by adding organic matter and nutrients, such as nitrogen, that are trapped by bacteria in the soil. Manure contains nitrogen (N) in inorganic and organic forms. Organic N is not available for crop growth until it is mineralized to ammonium (NH4+). Ammonium N is fairly building and available for plant uptake, but a portion is immobilized by microbial biomass and nitrifying bacteria convert NH4+ to nitrate (NO3−) which is subject to loss by leaching or denitrification and subsequent loss to the atmosphere. Volatile ammonia (NH3) in manure is transformed from NH4+ and can be lost to the atmosphere after land application. Nitrogen lost to the atmosphere is not available for crop production. In addition, ammonia (NH3) emission from livestock production causes undesirable environmental effects. Besides the undesirable effect of NH3, manure also comprises methane (CH4). Methane is a greenhouse gas and it is generally known that the emission of CH2 in the atmosphere should be reduced.

There is thus a need for a product that can be added to manure which can improve the quality of manure by providing an increase amount of nutrients, such as nitrogen, available to crops.

There is a need for a product that can be added to manure which can provide an improved fertilizing quality to crop plants.

In addition there is a need for a product that can be added to manure which helps to reduce the ammonia and/or methane emission in manure or in soil.

It is an object of this invention, amongst other objects, to provide a consortium of micro-organisms which can be added to manure, for improving the quality of manure.

Yet, it is an other object of this invention to provide a consortium of micro-organisms which can process the manure so that ammonia and/or methane emission is reduced.

Yet, it is an other object of this invention to provide a consortium of micro-organisms that can be used for improving manure so that the nitrogen availability to plants increases.

Yet, it is an object of this invention to provide a consortium of micro-organisms which can be added to the soil, for improving soil fertility.

It is an other object of this invention, to provide a bacteria, which forms part of the consortium that can provide the above objects.

This object, amongst other objects, is met, at least partially, if not completely by the bacteria or consortium as claimed in the annex.

Especially, this object is met at least partially, if not completely by a bacterium comprising a partial 16S rDNA nucleic acid sequence having more than 85% sequence identity to the sequences presented as SEQ ID NO:1, or the complement thereof. The inventor surprisingly found a new bacterium that resides in a consortium. The bacterium in the consortium and the consortium provide an improved quality to manure in a way that less ammonia and/or methane is emitted from manure, when compared with manure where this consortium is not added.

The partial 16S rDNA can be found using the 16S rDNA sequencing method as described in Hall, L., Doerr, K. A., Wohlfiel, S. L., Roberts, G. D., 2003. Evaluation of the MicroSeq system for identification of mycobacteria by 16S ribosomal DNA sequencing and its integration into a routine clinical mycobacteriology laboratory, J. Clinic. Microbiol. 4, 1447-1453, of which the reference is incorporated in its entirety. The PCR was performed on bacterial suspension with the following primers (sequences in 5' to 3' direction) 16S500F (tggagagtttgatcctggctcag) and 16S500R (taccgcggctgctggcac).

Sequence identity, as used herein, is defined as the number of identical consecutive aligned nucleotides, or amino acids, over the full length of the present sequences divided by the number of nucleotides, or amino acids, of the full length of the present sequences and multiplied by 100%. For example, a sequence with 80% identity to SEQ ID No. 1 comprises over the total length of 550 amino acids of SEQ ID No. 1 440 identical aligned consecutive amino acids, i.e., 440/550*100%=80%.

The invention is related to a newly found bacterium. A phylogenetic tree has been measured using the UPGMA algorithm (Unweighted Pair Group Method with Arithmetic Means) provided by the program of Bionumerics (from Applied Maths) measuring the PCT ribotype band sizes. It was found that the bacterium having a 16S rDNA sequence comprising SEQ ID NO:1 belongs to the genus *Bacteriodetes*. In one embodiment, the invention is related to a bacterium wherein the bacteria is a *bacteriodetes* sp.

In another embodiment, the invention is related to a bacterium wherein the bacterium is as is deposited at CBS under the deposit no CBS 134116, as deposited at CBS (Centraal Bureau voor Schimmelcultures (now named Westerdijk Fungal Biodiversity Institute and located at Uppsalalaan 8,3584 CT, Utrecht, The Netherlands) on 27 Nov. 2012 under the Budapest Treaty), wherein CBS 134116 is a *bacteriodetes*.

In yet another embodiment, the bacterium has a sequence identity which is at least 85, 86, 87, 88, 89, 90, 91, 92, 93, 94, 95, 96, 97, 98, 99, 100% identical with the sequence as is presented as SEQ ID NO:1. In a preferred embodiment, the bacterium has a sequence identity which is at least 99.7, 99.8, 99.9, 100% identical with the sequence as is presented as SEQ ID NO:1.

In one aspect, the invention is related to a consortium comprising a bacterium as described above. The consortium may further comprise yeast of the genus *Candida*, preferably *Candida boidinii* C. Ramírez and/or *Candida ethanolica* Rybárová, Stros & Kocková-Kratochvílová, and/or may further comprise the bacteria *Lactobacillus rhamnosus/casei, Acetobacter pasteurianus/lovaiensus* and/or *Rhodococcus facians/yunnanensis*.

The consortium may further comprise other lactic acid bacteria and other acetic acid bacteria.

In one embodiment, the consortium comprises one or more bacteria selected from the group consisting of *Lactobacillus rhamnosus, Lactobacillus casei, Lactobacillus ghanensis, Lactobacillus paracasei, Bacillus subtilis sensu stricto, Bacillus amyloliquefaciens, Bacillus atrophaeus, Bacillus vallismoritis, Bacillus mojavensis, Bacillus tequilensis, Bacillus siamensis,* and *Bacillus methylotrophicus.* In a preferred embodiment, the consortium comprises all these bacteria.

In one embodiment, the consortium improves manure and reduces the emission of ammonia and/or methane compared with manure where no consortium according to this invention is added. With manure is understood excrements of animals, and can be in a semi liquid state, such as slurry.

In one embodiment, the consortium improves soil and reduces the emission of ammonia and/or methane compared with soil where no consortium according to this invention is added. With soil is understood the loose covering of mineral particles that thinly overlie the earth's surface, such as the soil covering farm lands where crops are grown.

In another embodiment, the invention is related to a consortium as is deposited at the CBS, and has the deposit number CBS134115 as deposited at Centraal Bureau voor Schimmelcultures (now named Westerdijk Fungal Biodiversity Institute and located at Uppsalalaan 8,3584 CT, Utrecht, The Netherlands on 27 Nov. 2012 under the Budapest Treaty).

In another embodiment, the consortium according to the invention further comprises a saccharide, preferably a monosaccharide and/or disaccharide. It is thought that the saccharide provides an environment for the bacteria and yeast in the consortium, which provides a composition of the bacteria and yeasts with a ratio in a way that in manure the production of ammonia and/or methane decreases. It is thought that the consortium provides an environment in manure, which is not favourable for ammonia producing bacteria.

In yet another embodiment, the saccharide is derived from cane source or beat source and is preferably a cane molasses.

In another aspect, the invention is related to the use of SEQ ID NO:1 for detecting or identifying a bacterium having the nucleic acid sequence or at least 85% sequence identity with SEQ ID NO:1.

In another aspect, the invention is related to a consortium of micro-organisms that comprises micro-organisms that provide reduction of the emission of ammonia and/or methane (NH3) in manure, as can be found in a consortium as is deposited at CBS under the deposit no of CBS 134115.

In another aspect, the invention is related to the use of a bacterium according to the invention or a consortium according to the invention, for the reduction of nitrogen in manure. The use can, for example, be performed by spraying a solution comprising the bacterium or the consortium according to the invention on manure. This can, for example, be performed using a method and product as described in the patent application NL2009019 of which the reference is incorporated in its entirety.

The manure is preferably animal manure, coming from e.g. pigs, cows, poultry or horses.

In another aspect, the invention is related to the use of a bacterium according to the invention or a consortium according to the invention, for the reduction of nitrogen in soil. The use can, for example, be performed by spraying a solution comprising the bacterium or the consortium according to the invention on soil.

In another aspect the invention is related to a method for reducing the emission of ammonia and/or methane in manure comprising adding the bacteria or the consortium according to the invention to manure and incubating said bacteria or consortium for a sufficient time allowing to reduce the formation of ammonia and/or methane in the manure.

In another aspect the invention is related to a method for reducing the emission of ammonia and/or methane in soil comprising adding the bacteria or the consortium according to the invention to soil and incubating said bacteria or consortium for a sufficient time allowing to reduce the formation of ammonia and/or methane in the soil.

Another aspect according to the invention is the use of manure according to the invention as an organic fertilizer.

The consortium or the bacteria in the consortium according to the invention contribute to a reduced emission of ammonia. It is thought that more nitrogen is in a phase that can be used by plants, such as crop plants. It is surprisingly found that the consortium and the bacteria according to the invention can be used for improving manure or soil and that beside the reduction of ammonia is obtained, also the fertilizing properties of the manure or soil according to the invention is improved.

The advantages and embodiments as described for several aspects in the invention can be valid for the other aspects according to the invention.

The present invention will be further described in detail in the following example of preferred embodiments of the invention.

FIG. 1

Dendrograms of Cluster analysis based on pairwise similarities of the new found bacterium *Bacteroidetes phylum* (FIG. 1A) (CBS 134116). The numbers above show the amount of similarity measured using the similarity-based clustering using the method Unweighted pair-grouping (UP-GMA)

EXAMPLE 1

Test of Ammonia Emission in Manure of a Pig Farm

In two livestock buildings for pigs, measurement of ammonia emission have been performed. In one building, the device as described in patent application NL2009019 has been used to treat the slurry coming from the pigs. The consortium as deposited at CBS under no. CBS 134115, has been sprayed on the slurry excreted by the pigs in building 1. Building 2 comprised slurry that was not treated with the consortium.

In each building 80 pigs were kept and the measurement was performed over a period of 12 weeks. Each day a composition comprising the consortium is sprayed in building 1 during 12 weeks. NH3 emission has been measured during 24 hours using the norm NEN 2826 (NEN 2826, 1999: Luchtkwaliteit. Uitworp door stationaire puntbronnen. Monsterneming en bepaling van het gehalte aan gasvormig ammoniak) by taking samples using a gas washing bottle comprising an absorption liquid. The ammonia measurements were performed by performing an absorption method and wet chemical analysis.

The samples were taken during several cycli of weeks of the pigs and during several months of the year. Table 1 shows the results of the emission of ammonia. The manure that was treated with the consortium as deposited at CBS under no. CBS 134115 showed an average decrease of 35% ammonia emission in the manure compared with the manure from building 2. The measurements were taken in several seasons (summer, winter and autumn) and also on different growing stages of the pigs (12 weeks in total, and each period of two weeks counts for 1 stage).

In the setup of the measurement, the amount of animals, the ages and the weight of the animals were in both animal buildings similar.

TABLE 1

| | Emission of ammonia per year in kg/animal | | |
|---|---|---|---|
| Stage | Piggery 1 | Piggery 2 (control) | % reduction |
| 4 | 6.2 | 11.3 | 45 |
| 2 | 3.5 | 5.5 | 35 |
| 5 | 4.3 | 7.2 | 39 |
| 1 | 4.2 | 5.8 | 26 |
| 5 | 4.7 | 6.2 | 25 |
| 3 | 2.9 | 4.8 | 38 |
| Average | 6.8 | 4.3 | 35 |

EXAMPLE 2

Test of Methane Emission in Manure for a Pig Form

A similar setup as in example 1 was performed. The methane was measured by taking a sample and using the lung method according to the norm NEN-EN, during 24 h.

There was an average methane reduction of 19% found in two different farms.

Table 2 shows the results in one farm of the methane measurement in piggery 1, where the consortium mixture was added to the manure, compared with piggery 2 (control), where no consortium mixture was added.

TABLE 2

| | Piggery 1 | Piggery 2 | Stage |
|---|---|---|---|
| Methane ppm | 14.8 | 17.8 | 1 (summer) |
| Methane emission/animal/year (kg/animal/year) | 1.0 | 1.6 | 1 (summer) |
| Methane ppm | 37.0 | 52.6 | 2 (winter) |
| Methane emission/animal/year (kg/animal/year) | 1.9 | 3.9 | 2 (winter) |
| Methane ppm | 32 | 60.6 | 3 (spring) |
| Methane emission/animal/year (kg/animal/year) | 2.1 | 4.3 | 3 (spring) |

EXAMPLE 3

Identification of Consortium

A sample of the consortium as is deposited at CBS under the deposit no of NR CBS 134115 was analyzed in order to identify its components. The analysis was performed by BCCM™/LMG Identification Service in Gent, Belgium.

An aliquot of the sample (a few drops) was taken aseptically and was uniformly spread on:
  LMG medium nr. 66 (MRS) and incubated anaerobically at 37° C. for 1 day,
  LMG medium nr. 37 (RCM) and incubated anaerobically at ° C. for 1 day,
  LMG medium nr. 13 and incubated aerobically at 28° C. for 1 day,
  LMG medium nr. 185 (TSA) and incubated aerobically at 28° C. for 2 days.
    On the different media, different colony types were observed which were purified for further analyses.

Four of the purified colonies (t1, t2, t6, and t7) were subjected to DNA fingerprinting using AFLP™. AFLP™ is a PCR based technique for whole genome fingerprinting via the selective amplification of restriction fragments (Vos et al., Nucleic Acids Research 23: 4407-4414 (1995)). The primer combination E01/T11 (Keygene) was used.

Clusteranalysis of the AFLP™ DNA fingerprint with the reference AFLP™ DNA fingerprints of the lactic acid bacteria taxa (including bifidobacteria) identified the cultures as *Lactobacillus rhamnosus* (t1), *Lactobacillus casei* (t2), *Lactobacillus ghanensis* (t6), and *Lactobacillus paracasei* (t7). It should be noted that literature data indicate that the type strain of *Lactobacillus casei* belongs to the species *Lactobacillus zeae*. However, the judicial commission of the international committee on systemics of prokaryotes ruled that the name *Lactobacillus zeae* should not be used (Int. J. Syst. Evol. Microbiol. 58: 1764-1765, (2008)).

Two of the purified colonies (t3 and t4) were subjected to partial 16S rDNA sequence analysis. Total DNA was prepared according to the protocol of Niemann et al. (J. Appl. Microbiol. 82: 477-484 (1997)). A fragment of the 16S rDNA gene (corresponding to the positions 8-1541 in the *Escherichia coli* numbering system) was amplified by PCR using conserved primers. The PCR product was purified using the NucleoFast® 96 PCR Clean-up kit (Macherey-Nagel, Germany). Sequencing reactions were performed using the BigDye® XTerminatorT Purification Kit (Applied Biosystems, USA). Sequence assembly was performed by using the software package BioNumerics (Applied Maths, Belgium).

Phylogenetic analysis was performed using the software package Bionumerics (Applied Maths, Belgium) after including the consensus sequence in an alignment of small ribosomal subunit sequences collected from the international nucleotide sequence library EMBL.

A similarity matrix was created by homology calculation with a gap penalty of 0%; unknown bases were discarded. In this way, a similarity of ≥97%, being significant for possible species identification, was found with several validly described *Bacillus* species. However, the high sequence similarities (99.1-100%, based on a partial sequence) obtained with all validly described species of the *B. subtilis*-complex (a set highly related species, currently encompassing *B. subtilis sensu stricto*, *B. amyloliquefaciens*, *B. atrophaeus*, *B. vallismoritis*, *B. mojavensis*, *B. tequilensis*, *B. siamensis*, and *B. methylotrophicus*), indicate that that one of the cultures (t3) belongs to one of these species. For the other culture, a similarity of ≥97%, being significant for possible species identification, was found with several validly described *Lactobacillus* species. However, the high sequence similarities (99.6-99.7) based on a partial sequence) obtained with the type strains of *L. casei* (99.7%) and *L. zeae* (99.6%), indicate that this culture (t4) belongs to one of these species, in particular to *L. casei*.

For a further analysis of the sample, an aliquot was taken aseptically and a serial (decimal) dilution in physiological water was made. Aliquots of 0.1 ml were uniformly spread on:
  LMG medium nr. 185 (TSA)and incubated aerobically at 28° C. for 3 days.

One additional colony type (t8) was observed and purified for further analysis by partial 16S rDNA sequence analysis as described above. In this way, a similarity of ≥97%, being significant for possible species identification, was found with several validly described *Lactobacillus* species. however, the high sequence similarities (99.6-99.9%, based on a partial sequence) obtained with the type strains of both subspecies of *L. paracasei*, indicate that that this culture (t8) belongs to this species.

The invention claimed is:

1. A consortium of bacteria comprising the bacteria *Lactobacillus rhamnosus, Lactobacillus casei, Lactobacillus ghanensis, Lactobacillus paracasei*, one of *Bacillus subtilis sensu stricto, Bacillus amyloliquefaciens, Bacillus atrophaeus, Bacillus vallismortis, Bacillus mojavensis, Bacillus tequilensis, Bacillus siamensis*, and *Bacillus methylotrophicus*, and the bacterium deposited at CBS under deposit no. CBS 134116, wherein the consortium reduces the emission of ammonia and/or methane in manure or soil compared with manure or soil where the consortium has not been added, and wherein the consortium is deposited at CBS under the deposit no. CBS 134115.

2. The consortium according to claim 1, wherein the consortium further comprises a saccharide.

3. The consortium according to claim 2, wherein the saccharide is derived from a cane source or beet source.

4. The consortium according to claim 3, wherein the cane source is cane molasses.

5. The consortium according to claim 2, wherein the saccharide is a monosaccharide.

6. The consortium according to claim 2, wherein the saccharide is a disaccharide.

* * * * *

SEQUENCE LISTING

<160> NUMBER OF SEQ ID NOS: 1

<210> SEQ ID NO 1
<211> LENGTH: 498
<212> TYPE: DNA
<213> ORGANISM: Unknown
<220> FEATURE:
<221> NAME/KEY: source
<222> LOCATION: 1..498
<223> OTHER INFORMATION: /organism="Unknown"
      /note="New Bacteriodetes"
      /mol_type="unassigned DNA"

<400> SEQUENCE: 1

```
cctggctcag gatgaacgct agcggcaggc ttaatacatg caagtcgtgg ggcagcatga        60
atgtagcaat acatttgatg gcgaccggca aacgggtgcg gaacacgtac acaaccttcc       120
tataagtggg gaatagccca gagaaatttg gattaatacc ccgtaacata acgatgtggc       180
atcacattgt tattatagct tcggcgctta ttgatgggtg tgcggctgat tagatagttg       240
gcggggtaac ggcccaccaa gtctacgatc agtagctgat gtgagagcat gatcagccac       300
acgggcactg agacacgggc ccgactccta cgggaggcag cagtaaggaa tattggtcaa       360
tggacgcaag tctgaaccag ccatgccgcg tgaaggatta aggtcctctg gattgtaaac       420
ttcttttatc tgggacgaaa aaaggcgatt cttcgtcact tgacggtacc agatgaataa       480
gcaccggcta actccgtg                                                     498
```